(12) United States Patent
Dickstein et al.

(10) Patent No.: US 9,956,439 B2
(45) Date of Patent: May 1, 2018

(54) BREATHING EQUIPMENT TRAINING

(71) Applicant: Blast Mask, LLC, Dallas, TX (US)

(72) Inventors: Justin Clayton Dickstein, Dallas, TX (US); Michael R. Moussa, Euless, TX (US); Stephen Hilton Savoie, Everman, TX (US)

(73) Assignee: Blast Mask, LLC, Dallas, TX (US)

( * ) Notice: Subject to any disclaimer, the term of this patent is extended or adjusted under 35 U.S.C. 154(b) by 443 days.

(21) Appl. No.: 14/716,709

(22) Filed: May 19, 2015

(65) Prior Publication Data

US 2016/0089553 A1 Mar. 31, 2016

Related U.S. Application Data

(60) Provisional application No. 62/057,716, filed on Sep. 30, 2014.

(51) Int. Cl.
| | |
|---|---|
| *A62B 9/04* | (2006.01) |
| *A62B 18/02* | (2006.01) |
| *A62B 18/10* | (2006.01) |
| *A61M 16/20* | (2006.01) |
| *A63B 23/18* | (2006.01) |
| *A61M 16/06* | (2006.01) |

(52) U.S. Cl.
CPC .............. *A62B 18/02* (2013.01); *A62B 18/10* (2013.01); *A61M 16/06* (2013.01); *A61M 16/20* (2013.01); *A61M 16/208* (2013.01); *A63B 23/18* (2013.01)

(58) Field of Classification Search
CPC ....... A63B 23/18; A61M 16/06; A61M 16/20; A61M 16/205; A61M 16/206; A61M 16/208; A61M 16/209; A62B 18/00; A62B 18/02; A62B 18/025; A62B 18/04; A62B 18/06; A62B 18/08; A62B 18/10
See application file for complete search history.

(56) References Cited

U.S. PATENT DOCUMENTS

| | | | | |
|---|---|---|---|---|
| 2,642,574 A | * | 6/1953 | Eloranta | A42B 1/046 128/201.28 |
| 4,373,520 A | * | 2/1983 | Arbique | A62B 18/08 128/201.19 |
| 4,601,465 A | | 7/1986 | Roy | |

(Continued)

OTHER PUBLICATIONS

MSA—The Safety Company, "MSA G1 SCBA" manual, 16 pages, retrieval date May 8, 2015.

(Continued)

*Primary Examiner* — Joshua Lee

(57) ABSTRACT

An apparatus, breathing equipment training device, and method for breathing equipment training. The apparatus includes a shell and a diaphragm. The shell includes a first opening and a second opening. The first opening is configured to be inserted into a breathing opening in a mask to form a connection with the breathing opening of the mask. The diaphragm is inside the shell and positioned about the second opening. The diaphragm is configured to impede airflow into the shell through the second opening. The first opening can be defined by a first ellipse insertable into the breathing opening of the mask. The second opening can be defined by a second ellipse through which airflow enters into the shell. A diameter of the second ellipse can be greater than a diameter of the first ellipse.

18 Claims, 6 Drawing Sheets

(56) References Cited

U.S. PATENT DOCUMENTS

| | | | | |
|---|---|---|---|---|
| 4,850,346 A * | 7/1989 | Michel | ............... | A62B 18/025 |
| | | | | 128/206.15 |
| 5,924,420 A | 7/1999 | Reischel et al. | | |
| 6,554,746 B1 | 4/2003 | McConnell et al. | | |
| 8,342,179 B2 * | 1/2013 | Hacke | ............... | A61M 16/06 |
| | | | | 128/206.12 |
| 8,590,533 B2 * | 11/2013 | Danford | ............ | A63B 21/0004 |
| | | | | 128/201.22 |
| 2008/0178884 A1 * | 7/2008 | Gerson | ............... | A62B 9/02 |
| | | | | 128/206.15 |
| 2008/0257352 A1 * | 10/2008 | Penton | ............... | A62B 7/04 |
| | | | | 128/205.24 |
| 2010/0101584 A1 * | 4/2010 | Bledstein | ............... | A62B 18/10 |
| | | | | 128/863 |
| 2012/0094806 A1 | 4/2012 | Danford | | |
| 2012/0325205 A1 | 12/2012 | Allum et al. | | |
| 2013/0319420 A1 * | 12/2013 | Danford | ............... | A62B 18/10 |
| | | | | 128/206.21 |
| 2015/0040907 A1 * | 2/2015 | Hakim | ............... | A61M 16/0683 |
| | | | | 128/205.24 |
| 2016/0059049 A1 * | 3/2016 | Langford | ............... | A62B 9/04 |
| | | | | 128/205.27 |
| 2017/0120084 A1 * | 5/2017 | Tang | ............... | A62B 18/006 |

OTHER PUBLICATIONS

Drager Safety AG & Co. KGaA, "Drager FPS 7000 Full Face Mask", 2 pages, retrieval date May 8, 2015.

Scott Safety Technologies, Inc., "NFPA 2013 Edition Scott Products Scott Air-Pak and Accessories", 8 pages, retrieval date May 8, 2015.

Sperian RespiratoryProtection USA, LLC, "Warrior SCBA" 14 pages, retrieval date May 8, 2015.

Honeywell Safety Products, "Honeywell TITAN SCBA" 14 pages, retrieval date May 8, 2015.

Drager Safety AG & Co. KGaA, "Drager PSS 7000 Compressed Air Breathing Apparatus", 6 pages, retrieval date May 8, 2015.

The Toro Company, "Jar Top Valve Diaphragm (53804)" 2 pages, retrieval date May 8, 2015.

International Search Report and Written Opinion issued for PCT/US2015/059690 dated Feb. 4, 2016, 11 pgs.

* cited by examiner

BREATHING EQUIPMENT TRAINING

CROSS-REFERENCE TO RELATED APPLICATION(S) AND CLAIM OF PRIORITY

This application claims priority under 35 U.S.C. § 119(e) to U.S. Provisional Patent Application No. 62/057,716 filed on Sep. 30, 2014. The above-identified provisional patent application is hereby incorporated by reference in its entirety.

TECHNICAL FIELD

The present disclosure relates generally to training equipment. More particularly, the present disclosure relates to training devices and methods for breathing equipment.

BACKGROUND

People working in hostile and potentially hazardous environments, such as, for example, firemen, often use a self-contained breathing apparatus (SCBA) to breathe. For example, oxygen supply may be depleted in the potentially hazardous environment and/or the air in the potentially hazardous environment may not be fit for breathing. Given the risk and potentially hazardous nature, individuals should be properly trained to operate their equipment, such as the SCBA, and have the stamina necessary to perform difficult tasks before being subjected to entering and/or working in such environments.

Accordingly, it would be advantageous to have systems and methods that take into account one or more of the issues discussed above, as well as possibly other issues.

SUMMARY

Embodiments of the present disclosure provide an apparatus, breathing equipment training device, and method for breathing training.

In one example embodiment, an apparatus is provided. The apparatus includes a shell and a diaphragm. The shell includes a first opening and a second opening. The first opening is configured to be inserted into a breathing opening in a mask to form a connection with the breathing opening of the mask. The diaphragm is inside the shell and positioned about the second opening. The diaphragm is configured to impede airflow into the shell through the second opening.

In another example embodiment, a breathing equipment training device is provided. The breathing equipment training device includes a shell and a diaphragm. The shell includes a first opening, a second opening, and at least one latch. The shell is a single component that is airtight with an exception of the first and second openings. The first opening is configured to be inserted into a breathing opening in a mask and the at least one latch configured to fix the shell to the mask to form a connection with the breathing opening of the mask. The first opening is defined by a first circle insertable into the breathing opening of the mask. The second opening is defined by a second circle through which airflow enters into the shell. A diameter of the second circle is larger than a diameter of the first circle. The diaphragm is inside the shell positioned about the second circle of the second opening. The diaphragm is configured to impede airflow into the shell through the second opening In another example embodiment, a method for breathing equipment training is provided. The breathing equipment training device includes attaching, to a mask, a breathing equipment training device that includes (i) a shell including at least a first opening and a second opening, the first opening configured to be inserted into a breathing opening in the mask to form a connection with the breathing opening of the mask and (ii) a diaphragm inside the shell positioned about the second opening and configured to impede airflow into the shell through the second opening. The method also includes breathing through the breathing equipment training device.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

The various figures and embodiments used to describe the principles of the present disclosure in this patent document are by way of illustration only and should not be construed in any way to limit the scope of the present disclosure. Those skilled in the art will understand that the principles of the present disclosure may be implemented in any type of suitably-arranged device or system.

Various embodiments of the present disclosure recognize and take into account that, for safety reasons, people needing to use breathing equipment, such as, for example, firemen, construction workers, hazardous material response personnel, military personnel, underwater divers, etc., should first train with the equipment. For example, to preserve air supply, an SCBA utilizes on demand breathing. This means that the air flow does not continuously flow into the mask of the wearer of the SCBA. The wearer must suck or inhale into their mask in order to retrieve air from their air supply. Oftentimes, the amount of force that needs to be used to suck or inhale air into the air supply is substantial and/or not common for someone absent specific training.

Various embodiments of the present disclosure further recognize and take into account that use of air or oxygen tanks in the training of personnel to operate breathing equipment is costly. For example, training a person to breathe and suck or inhale properly with the breathing equipment can waste air in the tank when the ambient air is perfectly breathable. Accordingly, various embodiments of the present disclosure provide a breathing equipment training device and method that allow people to train to use breathing equipment without needing to have an air tank.

Figure 1:
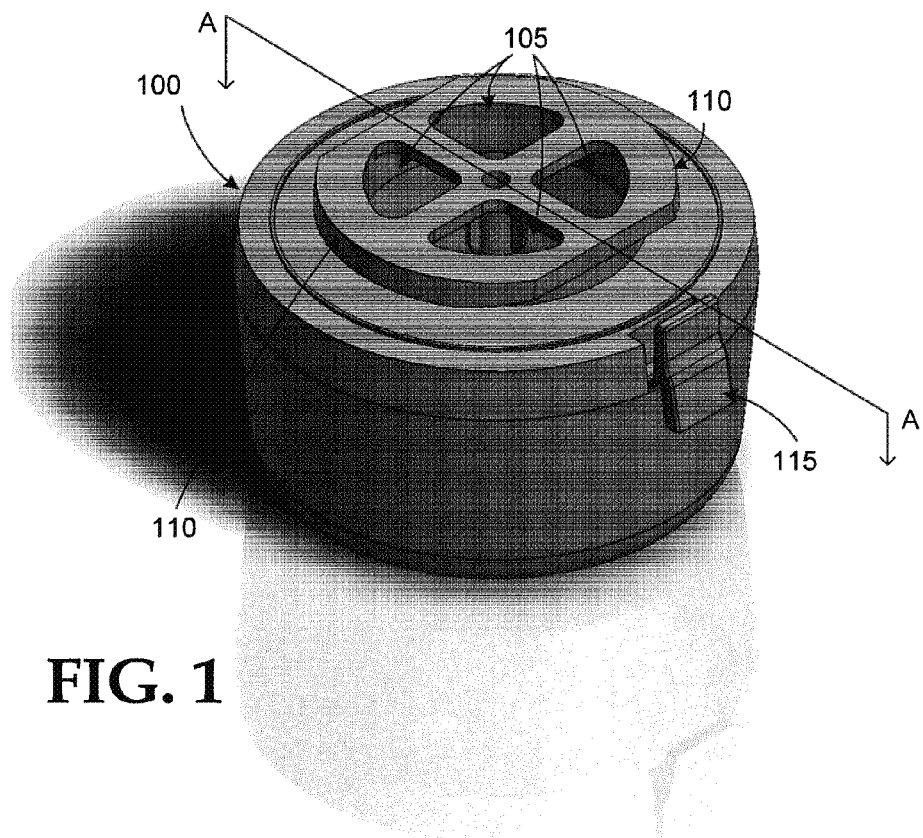
FIG. 1 illustrates a breathing equipment training device in accordance with various embodiments of the present disclosure.

FIG. 1 illustrates a breathing equipment training device 100 in accordance with various embodiments of the present disclosure. In this illustrative embodiment, breathing equipment training device 100 includes a cylindrically-shaped shell with a first set of openings 105 or holes designed to allow air to flow into a mask (e.g., mask 900 in FIG. 9) of an operator of breathing equipment, such as an SCBA. For example, the breathing equipment training device 100 may take the place of a regulator which is attached to the mask to regulate or otherwise control the flow of air into the mask. Breathing equipment training device 100 also includes a raised surface with a pair of flanges 110 that protrude from the breathing equipment training device 100. The flanges 110 are configured to be rotatably inserted into a slot or groove in the opening in the mask to couple or mate the breathing equipment training device 100 to the mask. Breathing equipment training device 100 also includes latch 115 which locks or fixes the breathing equipment training device 100 to the mask to deter or prevent the breathing equipment training device 100 from rotating inside the opening of the mask and becoming dislodged or disconnected. In this example embodiment, the shell of the breathing equipment training device 100 is a single component, one piece that is not segmentable except through cutting or otherwise destroying the shell. For example, the shell may be a molded plastic or other composite material.

Figure 2:
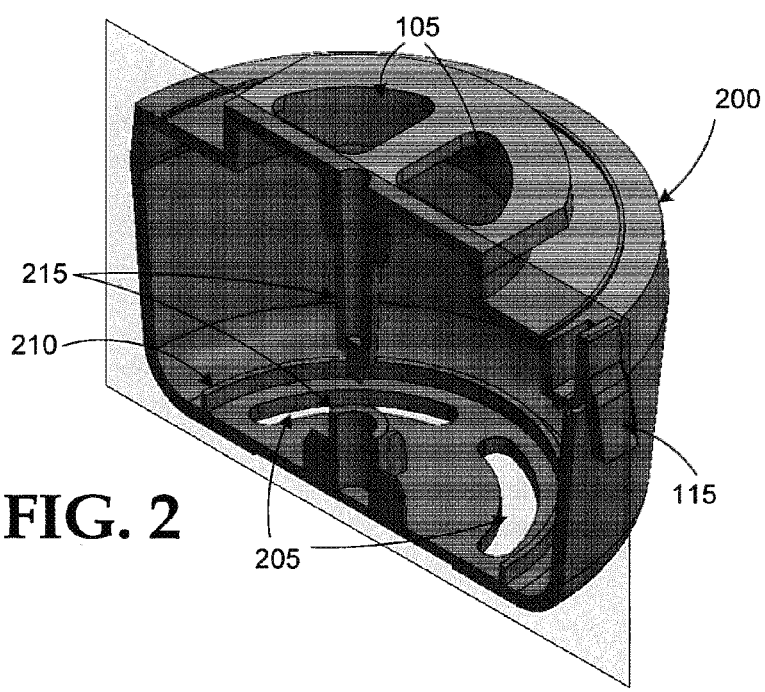
FIG. 2 illustrates a cross-sectional view of a shell for the breathing equipment training device illustrated in FIG. 1.

FIG. 2 illustrates a cross-sectional view of a shell for the breathing equipment training device illustrated in FIG. 1. In this illustrative embodiment, the shell 200 is seen opened along the cross section denoted by line AA in FIG. 1. As illustrated, the shell 200 has a second set of openings 205 or holes seen in the bottom of the shell 200. A raised ring 210 surrounds the second set of openings 205 in the shell 200. Though illustrated with four slot-shaped or circularly-shaped openings or holes, the first and second set of openings 105 and 205 may include any number of different openings or holes of any number of different shapes.

Shell 200 further includes pins 215 which are adapted to receive and hold a diaphragm or valve in place over the second set of openings 205. In this illustrative example, shell 200 does not include a diaphragm or valve as is included in the breathing equipment training device 100. An example diaphragm or valve is depicted in FIG. 8 and illustrated in a bottom portion of the breathing equipment training device 100 in FIG. 7. The diaphragm or valve covers the second set of openings 205 and is made of a flexible material so as to impede or resist (but not completely block) the flow of air and other fluids through the second set of openings 205. For example, the diaphragm or valve may be made from rubber, plastic, polyurethane, a composite material, etc.

In this manner, when attached to a mask, the breathing equipment training device 100 impedes or resists the flow of air into the mask, simulating usage of breathing equipment using on-demand breathing. Different types of diaphragms or valves having different levels of flexibility or resistance to air may be used to simulate, manage, and/or tune different levels of sucking or inhaling that may be required to operate the on-demand breathing equipment. For example, progressively stiffer diaphragms or valves may be inserted into the shell 200 of the breathing equipment training device 100 over time to increase the breathing strength and conditioning of the operator. Additionally, the tightness or snugness with which the diaphragm or valve fits within the shell 200 may be adjusted to simulate, manage, and/or tune different levels of resistance by, for example, increasing or decreasing a width of the diaphragm or valve and/or the shell 200.

Figure 3:
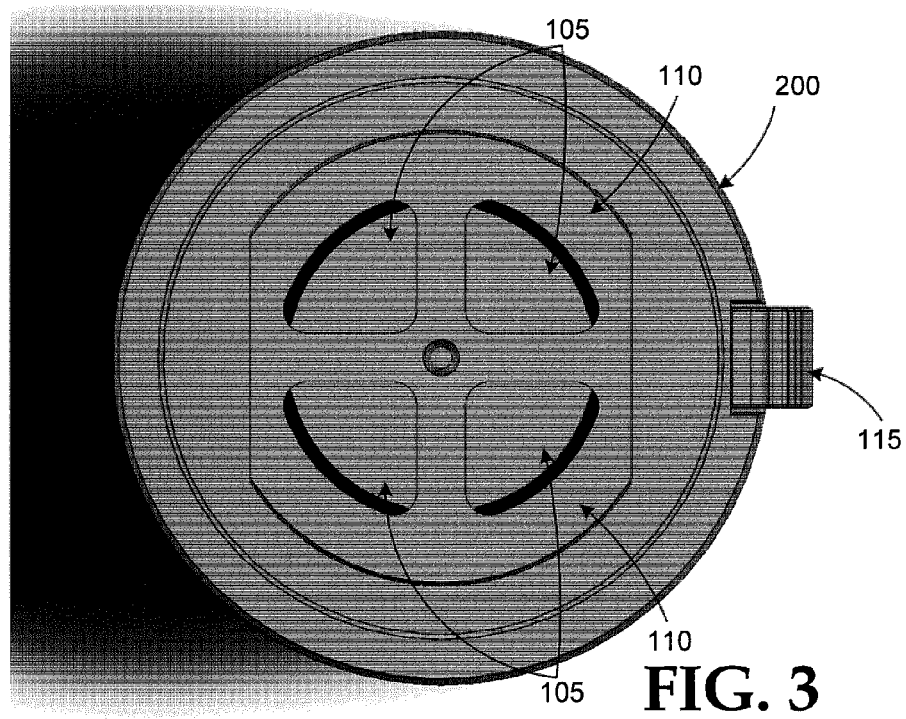
FIG. 3 illustrates a top view of a shell for a breathing equipment training device in accordance with various embodiments of the present disclosure.

FIG. 3 illustrates a top view of shell 200 for breathing equipment training device 100 in accordance with various embodiments of the present disclosure. In this view, the flanges 110, latch 115, and first set of openings 105 are seen.

Figure 4:
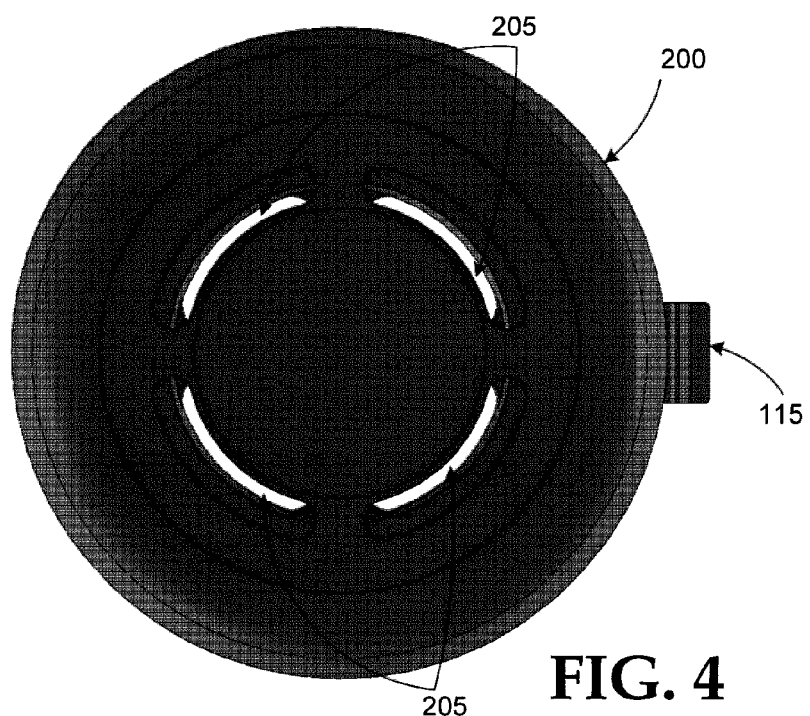
FIG. 4 illustrates a bottom view of a shell for a breathing equipment training device in accordance with various embodiments of the present disclosure.

FIG. 4 illustrates a bottom view of shell 200 for a breathing equipment training device 100 in accordance with various embodiments of the present disclosure. In this view, second set of openings 205 are seen, and through the second set of openings 205, the first set of openings 105 can be seen. In FIGS. 3 and 4, just the shell 200 is present. The diaphragm or valve is not present inside the shell 200. As can be seen, without the diaphragm or valve, air can freely pass through the second set of openings 205 into the shell 200 and out the first set of openings 105. While the terms "top" and "bottom" are used for the convenience of the reader, any side of the breathing equipment training device 100 may be the "top", "bottom", or "side" of the device 100 based on the orientation of the device 100 and the perspective of the viewer.

Figure 5:
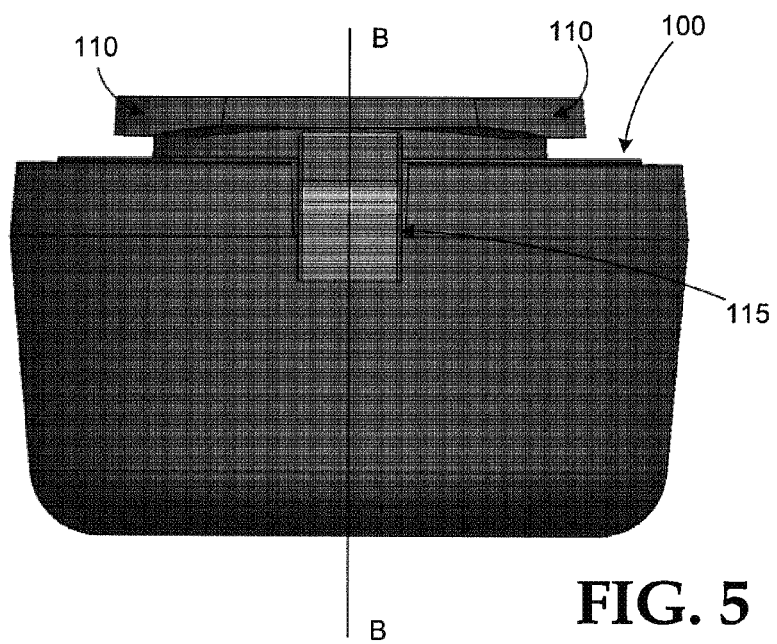
FIG. 5 illustrates a side view of a breathing equipment training device in accordance with various embodiments of the present disclosure.

FIG. 5 illustrates a side view of a breathing equipment training device 100 in accordance with various embodiments of the present disclosure. As illustrated, the flanges 110 protrude out from the raised surface of the breathing equipment training device 100 to connect, seal, or otherwise attach the breathing equipment training device 100 to a mask for breathing equipment.

Figure 6:
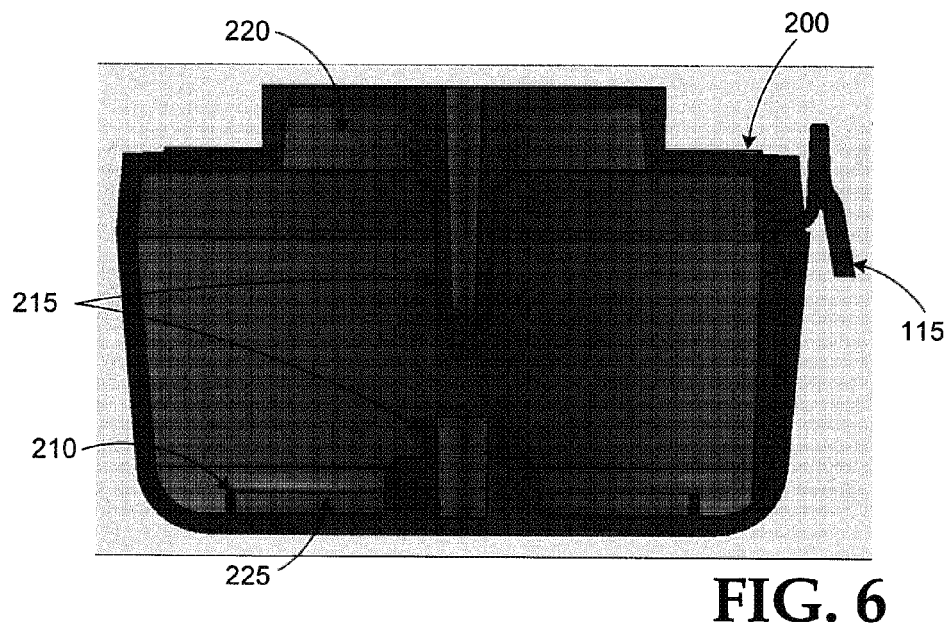
FIG. 6 illustrates a cross-sectional view of a shell for the breathing equipment training device illustrated in FIG. 5.

FIG. 6 illustrates a cross-sectional view of a shell 200 for the breathing equipment training device 100 illustrated in FIG. 5. In this illustrative embodiment, the shell 200 is seen opened along the cross section denoted by line BB in FIG. 5. FIG. 6 also illustrates an important concept of one or more embodiments of the present disclosure that the diameter of the ellipse or circle 220 defining the first opening 105 is smaller than the ellipse or circle 225 defining the second opening 205. For example, this configuration simulates a respirator that would be attached to the mask of an SCBA. Additionally, the larger diameter of the second opening 205 allows for more surface area for air to enter the mask, which improves the customization of simulating on-demand breathing. For example, the larger surface area of the area for the second opening 205 allows for openings in the second set of openings 205 to be larger and allow for more air to enter the shell 200, which allows for the customization of the shell 200 to more closely simulate the on-demand breathing associated with a respirator of an SCBA.

Figure 7:
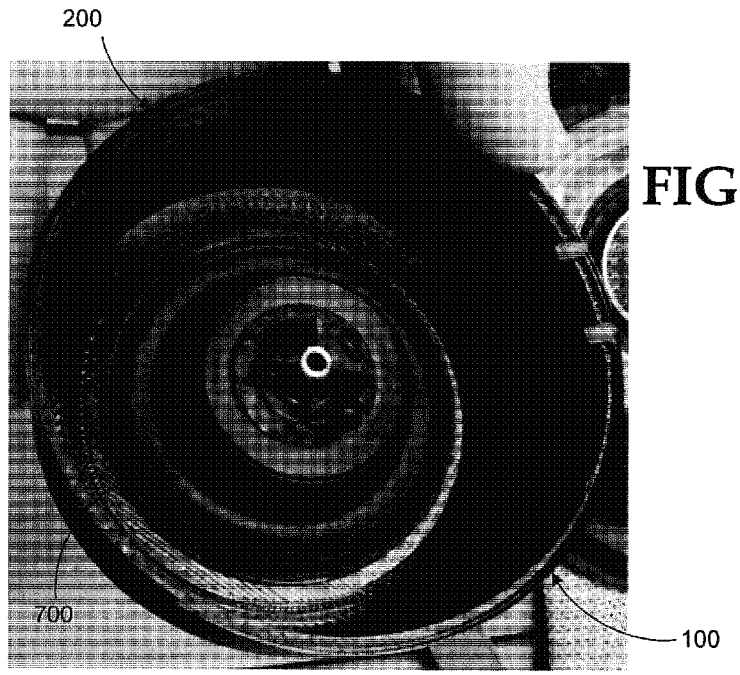
FIG. 7 is an image of the breathing equipment training device with a top portion removed.
Figure 8:
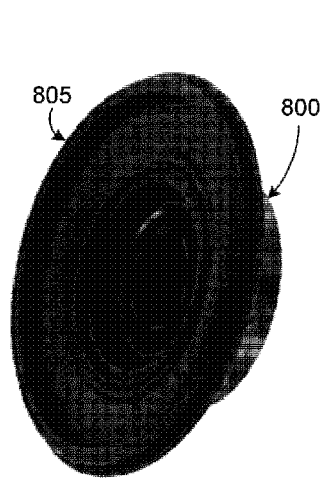
FIG. 8 illustrates a diaphragm insertable in a shell for the breathing equipment training device in accordance with an illustrative embodiment.

FIG. 7 is an image of the breathing equipment training device 100 with a top portion removed. In this illustrative embodiment, diaphragm or valve 700 is seen present inside the shell 200 of the device 100, because the top portion of the device 100 has been removed for illustration purposes. Diaphragm or valve 700 covers the second set of openings 205 (not seen in this view) in the bottom of the device 100. As illustrated, the diaphragm or valve 700 tapers outwardly towards the second set of openings 205. In this configuration, a strong sucking or inhaling action away from the second set of openings 205 by the operator of the device 100 can cause the tapered portions of the diaphragm or valve 700 to deform or bend slightly to allow the flow of air into the device 100 around the diaphragm or valve 700. In this illustrative embodiment, blowing or exhaling into the device 100 towards the second set of openings 205 (e.g., exhaling) may be much harder than sucking (e.g., inhaling) given the orientation and tapering of the diaphragm or valve 700 in the valve.

FIG. 8 illustrates a diaphragm 800 insertable in the shell 200 for the breathing equipment training device 100 in accordance with an illustrative embodiment. As illustrated, the diaphragm 800 is circularly shaped to cover the second set of openings 205 in the shell (not present in this view). The diaphragm 800 tapers in width from the center to the edges of the diaphragm 800. The diaphragm 800 also includes a ring 805 near and/or along the outer bottom edge of the diaphragm 800. This ring 805 acts as a seal and is matched to seat on or around the ring 210 in the shell 200. In this manner, the ring 805 on the diaphragm 800 and the ring in the shell 200 operate to provide substantially uniform resistance to breathing when operated to consistently and accurately simulate resistance provided by on-demand breathing equipment. While diaphragm 800, ring 805, and ring 210 are depicted as circular, any shape may be used (e.g., ellipse, oval, square, rectangular, etc.).

Figure 9:
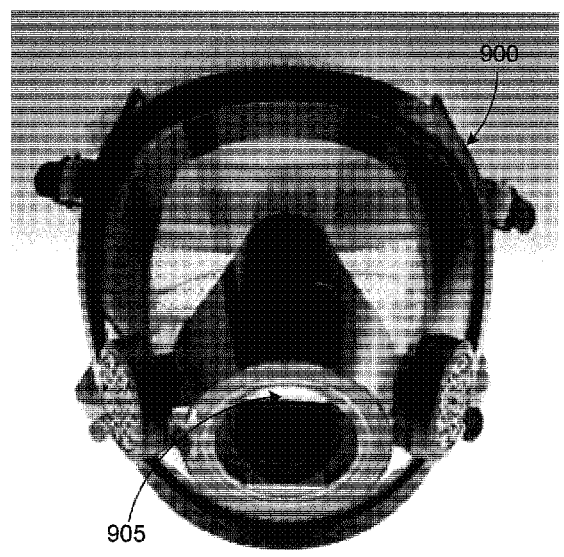
FIG. 9 illustrates a mask for an SCBA which may be utilized in implementing various embodiments of the present disclosure.

FIG. 9 illustrates a mask 900 for an SCBA, which may be utilized in implementing various embodiments of the present disclosure. The mask 900 is designed to be worn over the head and face of the operator to protect the eyes, nose, and mouth of the operator in hazardous environments and/or in environments where breathable ambient air is not present. Mask 900 includes a breathing opening 905 matched to be connected to a regulator or the breathing equipment training device 100 of the present disclosure.

Figure 10A:
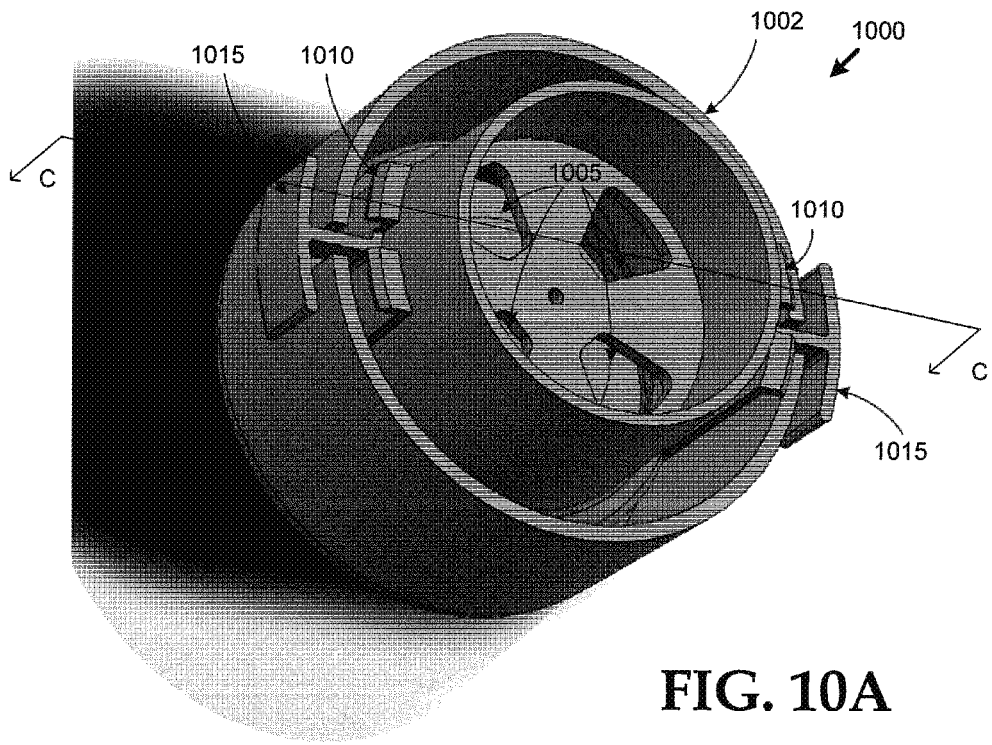
FIG. 10A illustrates another example of a breathing equipment training device in accordance with embodiments of the present disclosure.
Figure 11A:
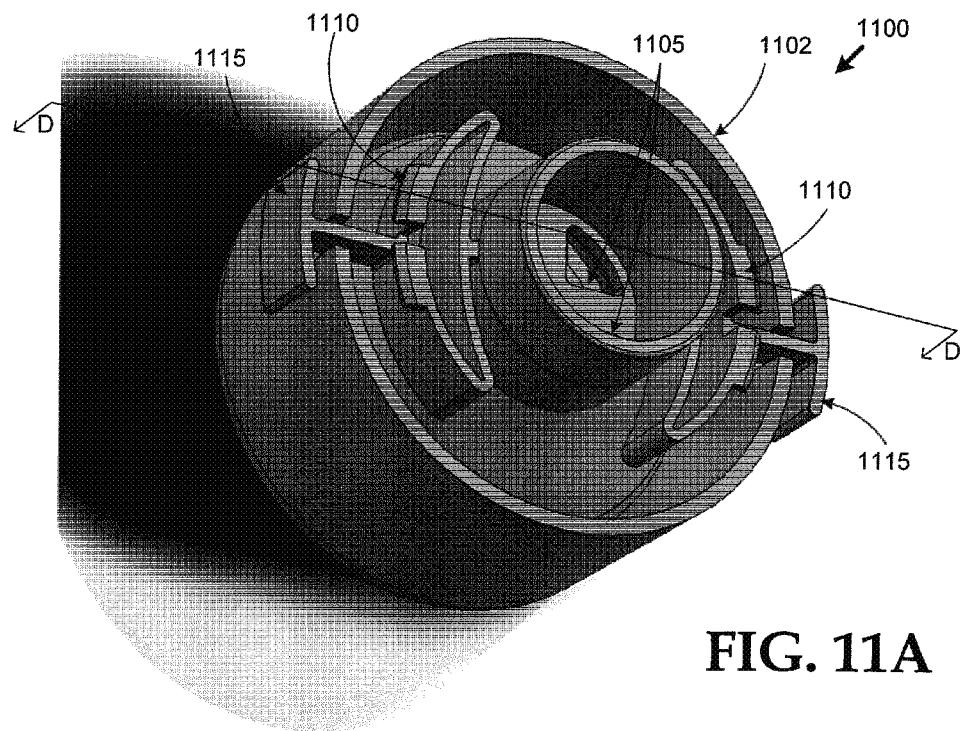
FIG. 11A illustrates another example of a breathing equipment training device in accordance with embodiments of the present disclosure.

FIG. 10A illustrates another example of a breathing equipment training device 1000 in accordance with embodiments of the present disclosure. For example, breathing equipment training device 1000 may be an example implementation of the breathing equipment training device 100 adapted to be inserted into a different type of mask than breathing equipment training device 100. While FIGS. 1, 10A, and 11A illustrate different examples of a breathing equipment training device adapted for use with a particular type of mask, any number of adaptations may be made to the area proximate to the first set of openings 105 to adapt the breathing equipment training device 100 to be inserted into or attached to any number of commercially-available masks.

In this illustrative embodiment, breathing equipment training device 1000 includes a cylindrically-shaped shell 1002 with a first set of openings 1005 or holes in a first opening designed to allow air to flow into a mask (e.g., mask 900 in FIG. 9) of an operator of breathing equipment, such as an SCBA. Breathing equipment training device 1000 also includes flanges 1010 attached to latches 1015, respectively. The flanges 1010 are configured to be inserted into or over slots, grooves, or protrusions, respectively, in the opening in the mask to couple or mate the breathing equipment training device 1000 to the mask. The latches 1015 are depressible to allow the flanges 1010 to be inserted into or removed from the mask for locking or fixing the breathing equipment training device 1000 to the mask. Once attached to the mask, the latches 1015 are also depressible to remove the breathing equipment training device 1000 from the mask.

Figure 10B:
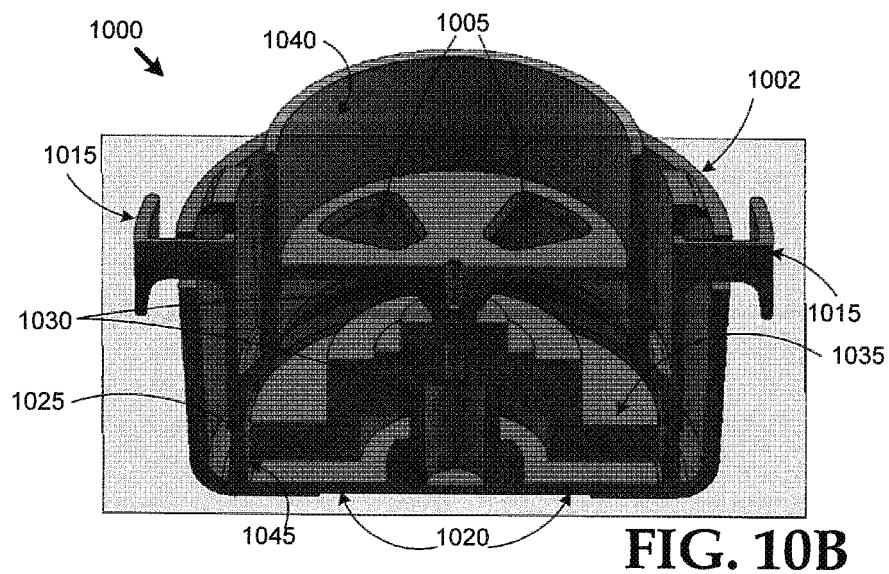
FIG. 10B illustrates a cross-sectional view of the breathing equipment training device illustrated in FIG. 10A.

FIG. 10B illustrates a cross-sectional view of the breathing equipment training device 1000 illustrated in FIG. 10A. In this illustrative embodiment, the breathing equipment training device 1000 is seen opened along the cross section denoted by line CC in FIG. 10A. As illustrated, the shell 1002 has a second set of openings 1020 seen in the bottom of the shell 1002. A ring 1025 surrounds the second set of openings 1020 in the shell 1002 and tapers upwardly toward the first set of openings 1005. Shell 1002 further includes pins 1030, which are adapted to receive and hold the diaphragm or valve 1035 in place over the second set of openings 1020. The diaphragm or valve 1035 may be one example of the diaphragm or valve 700 in FIG. 7.

In this illustrative embodiment, in addition to and/or in lieu of the ways of simulating, managing, and/or tuning different levels of resistance discussed above, different levels of inhalation and/or exhalation resistance may be achieved in breathing equipment training device 1000 by changing the distance between the surface of the shell 1002 proximate the second set of openings 1020 and the diaphragm or valve 1035. For example, the closer the diaphragm or valve 1035 is to the surface of the shell 1002 proximate the second set of openings 1020 the greater the inhalation and/or exhalation resistance becomes. In another example, the ring 1025 may taper inwardly or outwardly as the ring 1025 extends from the surface of the shell 1002 proximate the second set of openings 1020. In this manner, changing the distance between the surface of the shell 1002 proximate the second set of openings 1020 and the diaphragm or valve 1035 allows for adjustment and/or tuning of the tightness or looseness between the ring 1025 and the outer edge of the diaphragm or valve 1035, which also allows for additional or alternative ways of simulating, managing, and/or tuning different levels of inhalation and/or exhalation resistance by the breathing equipment training device 1000. In these examples, the diaphragm or valve 1035 is positioned about the second opening 1020, in that the diaphragm or valve 1035 controls, manages, resists, and/or impedes the flow of air into and out of the second opening 1020.

FIG. 10B also illustrates that the diameter of the ellipse or circle 1040 defining the first opening 1005 is smaller than the ellipse or circle 1045 defining the second opening 1020.

FIG. 11A illustrates another example of a breathing equipment training device 1100 in accordance with embodiments of the present disclosure. For example, breathing equipment training device 1100 may be an example implementation of the breathing equipment training device 100 or 1000 adapted to be inserted into a different type of mask than breathing equipment training device 100 or 1000. In this illustrative embodiment, breathing equipment training device 1100 includes a cylindrically-shaped shell 1102 with a first set of openings 1105 in a first opening designed to allow air to flow into a mask (e.g., mask 900 in FIG. 9) of an operator of breathing equipment, such as an SCBA. Breathing equipment training device 1100 also includes flanges 1110 attached to latches 1115, respectively. The flanges 1110 are configured to be inserted into or over slots, grooves, or protrusions, respectively, in the opening in the mask to couple or mate the breathing equipment training device 1100 to the mask. The latches 1115 are depressible to allow the flanges 1110 to be inserted into or removed from the mask for locking or fixing the breathing equipment training device 1100 to the mask. Once attached to the mask, the latches 1115 are also depressible to remove the breathing equipment training device 1100 from the mask.

Figure 11B:
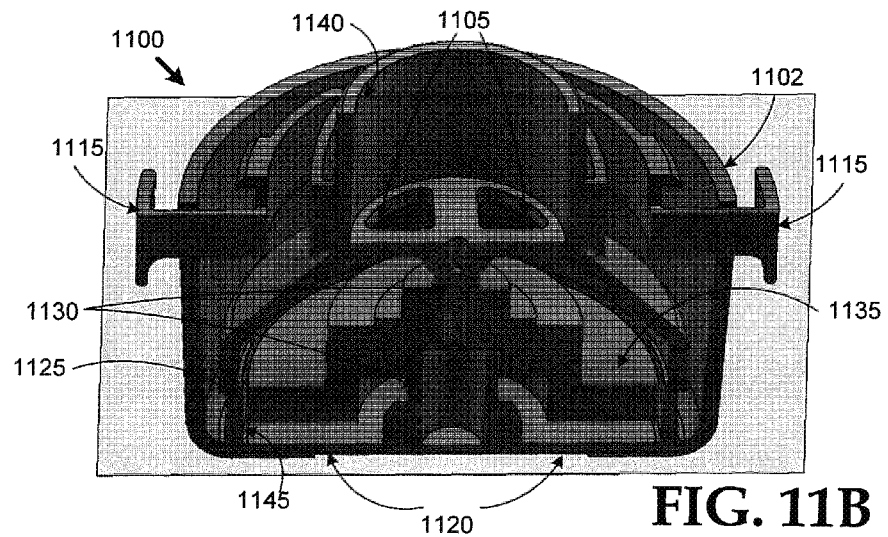
FIG. 11B illustrates a cross-sectional view of the breathing equipment training device illustrated in FIG. 11A.

FIG. 11B illustrates a cross-sectional view of the breathing equipment training device 1100 illustrated in FIG. 11A. In this illustrative embodiment, the breathing equipment training device 1100 is seen opened along the cross section denoted by line DD in FIG. 11A. As illustrated, the shell 1102 has a second set of openings 1120 seen in the bottom of the shell 1102. A ring 1125 surrounds the second set of openings 1120 in the shell 1102 and tapers upwardly toward the first set of openings 1105. Shell 1102 further includes pins 1130, which are adapted to receive and hold the diaphragm or valve 1135 in place over the second set of openings 1120. The diaphragm or valve 1135 may be one example of the diaphragm or valve 700 in FIG. 7.

In this illustrative embodiment, in addition to and/or in lieu of the ways of simulating, managing, and/or tuning different levels of resistance discussed above, different levels of inhalation and/or exhalation resistance may be achieved in breathing equipment training device 1100 by changing the distance between the surface of the shell 1102 proximate the second set of openings 1120 and the diaphragm or valve 1135. For example, the closer the diaphragm or valve 1135 is to the surface of the shell 1102 proximate the second set of openings 1120 the greater the inhalation and/or exhalation resistance becomes. In another example, the ring 1125 may taper inwardly or outwardly as the ring 1125 extends from the surface of the shell 1102 proximate the second set of openings 1120. In this manner, changing the distance between the surface of the shell 1102 proximate the second set of openings 1120 and the diaphragm or valve 1135 allows for adjustment and/or tuning of the tightness or looseness between the ring 1125 and the outer edge of the diaphragm or valve 1135, which also allows for additional or alternative ways of simulating, managing, and/or tuning different levels of inhalation and/or exhalation resistance by the breathing equipment training device 1100. In these examples, the diaphragm or valve 1135 is positioned about the second opening 1120, in that the diaphragm or valve 1135 controls, manages, resists, and/or impedes the flow of air into and out of the second opening 1120.

FIG. 11B also illustrates that the diameter of the ellipse or circle 1140 defining the first opening 1105 is smaller than the ellipse or circle 1145 defining the second opening 1120.

Embodiments of the present disclosure also include a method of training to use breathing equipment. In addition to the description above, the method includes attaching the breathing equipment training device 100 to a mask, e.g., mask 900 of breathing equipment, for example, an SCBA. The method further includes breathing through the mask 900 and the breathing equipment training device 100 to train for the on-demand breathing experienced using certain types of breathing equipment. For example, the training may include performing exercises to increase the stamina of the wearer of the breathing equipment training device.

In one or more embodiments, the breathing equipment training device 100 may be a molded plastic device that looks, feels, and weighs about the same as an SCBA regulator. For example, the breathing equipment training device 100 may connect to and secure to the face piece the same as a regulator, and the interior components have a pressure demand—type of inspiration and exhalation valve or components that require the same deliberate breathing efforts as a regular SCBA, without needing to use the air supply of an SCBA.

Most training for use of an SCBA does not require the trainee to need a supply of air, though it is beneficial in realistic training. For example, while wearing an SCBA, a user may need to perform tasks that have a high level of exertion, while the on-demand breathing from the SCBA can make breathing and oxygen supply more difficult than breathing without the SCBA. Embodiments of the present disclosure give the trainee all the physical sensations and demands of being attached to an on-demand air supply without actually using an air supply. This eliminates the need for time consuming, labor-intensive, and costly air refilling support operations, while allowing individuals to be exposed to the demands of SCBA breathing to increase preparedness and stamina.

While various embodiments are described as use of the device 100 in connection with training to use equipment such as an SCBA, in other embodiments, the device 100 may be used in connection with a mask for the purposes of increasing stamina or endurance unrelated to use of equipment such as an SCBA, such as, for example, fitness, cardiovascular, or high-altitude training. In other examples, the device may be used to simulate underwater breathing. For example, the SCBA may be a self-contained underwater breathing apparatus (SCUBA) and the device 100 may be used to simulate and train for on-demand breathing experienced underwater with SCUBA equipment.

It may be advantageous to set forth definitions of certain words and phrases used throughout this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following: A, B, and C; A and B; A and C; B and C; A; B; and C.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An apparatus comprising:
   a shell including a first opening and a second opening, the first opening configured to be inserted into a breathing opening in a mask to form a connection with the breathing opening of the mask; and
   a diaphragm inside the shell positioned about the second opening and configured to impede airflow into the shell through the second opening, wherein the shell further includes a pair of pins contacting the diaphragm on opposite sides of the diaphragm to hold the diaphragm in position about the second opening, a first of the pins positioned adjacent to the first opening and a second of the pins positioned adjacent to the second opening, and wherein the shell further includes at least one depressible latch positioned on an outer surface of the shell accessible after formation of the connection with the mask, the at least one depressible latch configured to fix the shell to the mask.

2. The apparatus of claim 1, wherein:

the first opening is defined by a first ellipse insertable into the breathing opening of the mask, the second opening is defined by a second ellipse through which airflow enters into the shell, and a diameter of the second ellipse is greater than a diameter of the first ellipse.

3. The apparatus of claim 2, wherein the first opening comprises a first plurality of holes and the second opening comprises a second plurality of holes.

4. The apparatus of claim 2, wherein the first and second ellipses are circles.

5. The apparatus of claim 1, wherein the shell is a single component that is airtight between the first and second openings with an exception of the first and second openings.

6. The apparatus of claim 1, wherein the diaphragm tapers outwardly towards a surface of the second opening.

7. The apparatus of claim 1, wherein the diaphragm includes a ring on a surface of the diaphragm proximate to the second opening, the ring surrounding the opening on an interior surface of the shell, the ring configured to impede airflow from the first opening out of the shell through the second opening and to impede airflow into the shell from the second opening toward the first opening.

8. A system comprising the apparatus of claim 1, the system further comprising the mask configured to cover a mouth and nose of a user, the mask including the breathing opening configured to allow airflow into the mouth of the user.

9. The system of claim 8, wherein the mask is a component of a self-contained breathing apparatus.

10. A breathing equipment training device, the device comprising:

a shell including a first opening, a second opening, a pair of pins, and at least one depressible latch, the shell being a single component that is airtight between the first and second openings with an exception of the first and second openings, the first opening configured to be inserted into a breathing opening in a mask, the at least one depressible latch configured to fix the shell to the mask to form a connection with the breathing opening of the mask and positioned on an outer surface of the shell accessible after formation of the connection with the mask, the first opening defined by a first circle insertable into the breathing opening of the mask, the second opening defined by a second circle through which airflow enters into the shell, a diameter of the second circle being larger than a diameter of the first circle; and a diaphragm inside the shell positioned about the second circle of the second opening and configured to impede airflow into the shell through the second opening, wherein the pair of pins contact the diaphragm on opposite sides of the diaphragm to hold the diaphragm in position about the second opening, a first of the pins positioned adjacent to the first opening and a second of the pins positioned adjacent to the second opening.

11. The device of claim 10, wherein the first opening comprises a first plurality of holes and the second opening comprises a second plurality of holes.

12. The device of claim 10, wherein the diaphragm tapers outwardly towards a surface of the second opening.

13. The device of claim 12, wherein the diaphragm includes a ring on a surface of the diaphragm proximate to the second opening, the ring surrounding the opening on an interior surface of the shell, the ring configured to impede airflow from the first opening out of the shell through the second opening and to impede airflow into the shell from the second opening toward the first opening.

14. A system comprising the device of claim 10, the system further comprising the mask configured to cover a mouth and nose of a user, the mask including the breathing opening configured to allow airflow into the mouth of the user.

15. The system of claim 14, wherein the mask is a component of a self-contained breathing apparatus.

16. A method for breathing equipment training, the method comprising:

attaching, to a mask, a breathing equipment training device that includes (i) a shell including at least a first opening and a second opening, the first opening configured to be inserted into a breathing opening in the mask to form a connection with the breathing opening of the mask and (ii) a diaphragm inside the shell positioned about the second opening and configured to impede airflow into the shell through the second opening;

fixing the breathing equipment training device to the mask using two depressible latches, each latch on opposite sides of an outer surface of the shell, the latches accessible after formation of the connection with the mask; and breathing through the breathing equipment training device, wherein the shell further includes a pair of pins contacting the diaphragm on opposite sides of the diaphragm to hold the diaphragm in position about the second opening, a first of the pins positioned adjacent to the first opening and a second of the pins positioned adjacent to the second opening.

17. The method of claim 16, wherein breathing through the breathing equipment training device comprises simulating on-demand breathing associated with a self-contained breathing apparatus.

18. The method of claim 16, wherein the mask is a component of a self-contained breathing apparatus.

* * * * *